United States Patent
Wood et al.

[11] Patent Number: 6,040,455
[45] Date of Patent: Mar. 21, 2000

[54] ONE-POT PROCESS FOR THE PREPARATION OF 5-SULFONYL-SUBSTITUTED BENZOTRIAZOLES UV ABSORBERS

[75] Inventors: Mervin G. Wood, Poughquag, N.Y.; William Wiggins, Mobile, Ala.; Catherine Blake, Saraland, Ala.; Albert Carpenter, Mobile, Ala.; Wha Chen, Freemont, Calif.

[73] Assignee: Ciba Specialty Chemicals Corporation, Tarrytown, N.Y.

[21] Appl. No.: 09/234,879

[22] Filed: Jan. 21, 1999

[51] Int. Cl.[7] .................................................. C07D 249/20
[52] U.S. Cl. ......................... 548/259; 544/132; 544/366; 546/199
[58] Field of Search .............................................. 548/259

[56] References Cited

U.S. PATENT DOCUMENTS

| | | | |
|---|---|---|---|
| 3,004,896 | 10/1961 | Heller et al. | 167/90 |
| 3,218,332 | 11/1965 | Heller et al. | 260/308 |
| 3,766,205 | 10/1973 | Heller et al. | 260/308 |
| 5,280,124 | 1/1994 | Winter et al. | 548/259 |
| 5,319,091 | 6/1994 | DesLauriers et al. | 548/259 |
| 5,436,349 | 7/1995 | Winter et al. | 548/259 |

FOREIGN PATENT DOCUMENTS 62-288630  12/1987  Japan.

*Primary Examiner*—Patricia L. Morris
*Attorney, Agent, or Firm*—Luther A. R. Hall

[57] ABSTRACT

5-Sulfonyl substituted benzotriazole UV absorbers are prepared from the corresponding 5-chlorobenzotriazole in a two step, but one-pot process where the second step involves the oxidation of the non-isolated 5-thio substituted benzotriazole using sodium tungstate, hydrogen peroxide and formic acid. The 5-sulfonyl substituted benzotriazoles exhibit enhanced absorption in the near-visible range (over 350 nm) thus providing effective protection to substrates in this critical area of the spectrum.

18 Claims, No Drawings

ONE-POT PROCESS FOR THE PREPARATION OF 5-SULFONYL-SUBSTITUTED BENZOTRIAZOLES UV ABSORBERS

The instant invention pertains to a novel process for the preparation of 5-sulfonyl substituted benzotriazole UV absorbers from the corresponding 5-chlorobenzotriazole precursors in a two-step, but one pot process.

BACKGROUND OF THE INVENTION

The 5-sulfonyl substituted benzotriazole UV absorbers are useful for the stabilization of polymer systems against the harmful effects of UV and actinic light. These compounds and their compositions and applications are described more particularly in U.S. Pat. Nos. 5,280,124 and 5,436,349. Some sulfone-containing benzotriazoles are described in earlier patents by H-J. Heller et al., Swiss Patent No. 355,947, and U.S. Pat. Nos. 3,218,332 and 3,766,205. According to U.S. Pat. No. 3,766,205, a 5-thio derivative was synthesized from the corresponding sulfonic acid. The sulfonic acid was converted to its sulfonyl chloride which in turn is reduced to a thiol group and added to an acrylate ester to give the corresponding thiopropionate derivative.

The instant invention describes an improved process for the manufacture of 5-sulfonyl substituted benzotriazoles starting from the corresponding 5-chlorobenzotriazoles. This synthetic route has been mentioned by Kobayashi et al., Japanese Sho 62-288,630 and DesLauriers et al. in U.S. Pat. No. 5,319,091. In the Kobayashi case, the desired compounds are polymeric thioether derivatives of benzotriazoles and not the corresponding sulfonyl derivatives.

Kobayashi et al. describe a method of preparing polyarene thioethers in which benzotriazole moieties are covalently attached to the polymer via a thioether linkage. These transformations are carried out under aqueous, strongly alkaline conditions at temperatures of 200–290° C. for a period of 20 minutes to 20 hours with preferably an organic amide present. The instant invention uses small non-polymeric thiol compounds at temperatures from 30–180° C. in the presence of an alkali metal hydroxide in polar aprotic solvents. Additonally, Kobayashi et al. state "It is preferably from the viewpoint of stability of the polymer that the above-mentioned organic amide solution contain water in an amount of 2.5 to 25 parts by weight and that the obtained aqueous solution have strong alkaline properties. For example, in the case of the above-mentioned solvent is diluted with a tenfold quantity of water, it is recommended that the alkaline strength of the aqueous solution have a pH exceeding 9.5." See Japanese Sho 62-288,630, page 15.

In the present invention, additional water is not needed. In fact, the desired reaction can be done under anhydrous conditions giving high yields with excellent product quality. The above-mentioned addition of a tenfold quantity of water could complicate and hinder recovery and recycle of the polar aprotic solvent which is needed for economical and ecological reasons. Clearly, the instant process is outside the disclosure of Kobayashi et al.

DesLauriers et al. in U.S. Pat. No. 5,319,091 describe a process for preparing sulfur-containing derivatives of 2-(2-hydroxyphenyl)-2H-benzotriazoles. In their process, sulfur-containing aromatic compounds are reacted with chloro-substituted 2-(2-hydroxyphenyl)-2H-benzotriazoles to yield an aryl sulfide derivative. These aryl sulfide compounds are then contacted with oxidizing agents to give the corresponding aryl sulfone 2-(2-hydroxyphenyl)-2H-benzotriazoles. DesLauriers et al. describe a process for contacting sulfur-containing aromatic compounds with a halosubstituted 2-(2-hydroxyphenyl)-2H-benzotriazole. The instant process can employ sulfur-containing aryl or alkyl compounds giving a more versatile dimension to the present invention. A direct comparison of the instant and DesLauriers processes are given in Example 4 and illustrate the unexpected superior results obtained by the instant process.

DesLauriers et al. isolate the intermediate aryl sulfide and dry it before proceeding with the oxidation step. In the instant process, isolation of this intermediate is not required. In fact, a much improved yield is obtained when the intermediate is not isolated. In working Examples 2–3 of U.S. Pat. No. 5,319,091, the final yields the aryl sulfone 2-(2-hydroxyphenyl)-2H-benzotriazole compound relative to the starting benzotriazole 5-chloro reactant are 65% and 60.1%. The instant process gives a yield of 88.6% for the same product as seen in instant Example 1.

DesLauriers et al. report a step 1 yield of 72.6% for the isolation of the thioether intermediate in Example 1 of U.S. Pat. No. 5,319,091. The instant process yields the same thioether intermediate in a 97% yield, but isolation of this intermediate is not required in the instant process.

DesLauriers et al. oxidize the thioether derivative with either m-chloroperbenzoic acid (MCPBA) in methylene chloride or with hydrogen peroxide and tungstic acid ($H_2WO_4$) in isopropanol. It is noted that, first, the use of MCPBA on an industrial scale has considerable disadvantages. These include the recovery and reuse of the waste m-chlorobenzoic acid which is a byproduct of this process. This recovery and reuse would be required to make this process economically and/or environmentally feasible. Second, using hydrogen peroxide, tungstic acid and isopropanol requires a reaction time of 12 hours. Even after 12 hours, 4.6% of 5-phenylsulfinyl-2-(2-hydroxy-3,5-di-tert-butyl-phenyl)-2H-benzotriazole and 0.8% of 5-phenylthio-2-(2-hydroxy-3,5-di-tert-butyl-phenyl)-2H-benzotriazole still remain.

On the other hand, the instant process using hydrogen peroxide, formic acid and sodium tungstate ($Na_2WO_4$) in xylene requires only two hours or less of reaction time. High isolated yields (97%) and excellent product quality are obtained. Unexpectedly, when in the preferred oxidizing system the formic acid is replaced with acetic acid, only a 60% conversion to sulfoxide and virtually no sulfone product is obtained. Peracetic acid (hydrogen peroxide in acetic acid) is mentioned as a suitable oxidizing agent by DesLauriers et al. in U.S. Pat. No. 5,391,091.

DETAILED DISCLOSURE

The instant invention pertains to a one-pot, two-step process for the preparation of 5-sulfonyl substituted benzotriazole UV absorbers where isolation of the 5-thio substituted intermediate is not required.

More particularly, the instant process pertains to the preparation of a compound of formula A, B, C or D

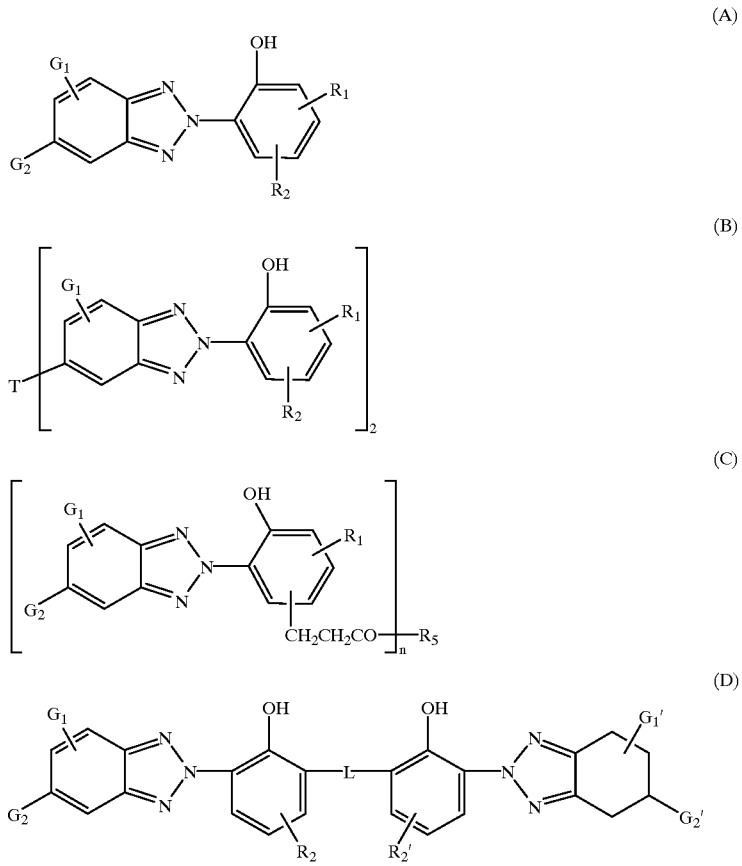

(A)

(B)

(C)

(D)

wherein $G_1$, $G_1'$, $G_2$ and $G_2'$ are independently hydrogen, halogen, nitro, cyano, $R_3SO—$, $R_3SO_2—$, $—COOG_3$, perfluoroalkyl of 1 to 12 carbon atoms, $—CO—G_3$, $—CO—NH—G_3$ or $—CO—N(G_3)_2$, $G_3$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms, with the proviso that at least one of $G_1$, $G_1'$, $G_2$ and $G_2'$ is $R_3SO_2$, $R_1$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms, $R_2$ and $R_2'$ are independently straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $R_2$ is hydroxyl or $—OR_4$ where $R_4$ is straight or branched chain alkyl of 1 to 24 carbon atoms; or said alkyl substituted by one or more $—OH$, $—OCO—R_{11}$, $—OR_4$, $—NCO$, $—NH_2$ or $—N(R_4)_2$ groups or mixtures thereof; or said alkyl or said alkenyl interrupted by one or more $—O—$, $—NH—$ or $—NR_4—$ groups or mixtures thereof and which can be unsubstituted or substituted by one or more $—OH$, $—OR_4$ or $—NH_2$ groups or mixtures thereof; or $R_2$ is $—SR_3$, $NH_2$, $—NHR_3$, $—N(R_3)_2$, $R_3SO—$ or $R_3SO_2—$; or $R_2$ is

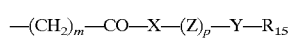

wherein

X is $—O—$ or $—N(R_{16})—$,

Y is $—O—$ or $—N(R_{17})—$,

Z is $C_2$-$C_{12}$-alkylene, $C_4$-$C_{12}$-alkylene interrupted by one to three nitrogen atoms, oxygen atoms or a mixture thereof, or is $C_3$-$C_{12}$-alkylene, butenylene, butynylene, cyclohexylene or phenylene, each substituted by a hydroxyl group, m is zero, 1 or 2, p is 1, or p is also zero when X and Y are $—N(R_{16})—$ and $—N(R_{17})—$, respectively, $R_{15}$ is a group $—CO—C(R_{18})=C(H)R_{19}$ or, when Y is $—N(R_{17})—$, forms together with $R_{17}$ a group $—CO—CH=CH—CO—$, wherein $R_{18}$ is hydrogen or methyl, and $R_{19}$ is hydrogen, methyl or $—CO—X—R_{20}$, wherein $R_{20}$ is hydrogen, $C_1$-$C_{12}$-alkyl or a group of the formula.

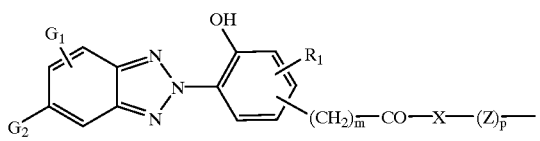

wherein the symbols $R_1$, X, Z, m and p have the meanings defined above, and $R_{16}$ and $R_{17}$ independently of one another are hydrogen, $C_1$-$C_{12}$-alkyl, $C_3$-$C_{12}$-alkyl interrupted by 1 to 3 oxygen atoms, or is cyclohexyl or $C_7$–$C_{15}$aralkyl, and $R_{16}$ together with $R_{17}$ in the case where Z is ethylene, also forms ethylene, n is 1 or 2, when n is 1, $R_5$ is Cl, $OR_6$ or $NR_7R_8$, or $R_5$ is —$PO(OR_{12})_2$, —$OSi(R_{11})_3$ or —OCO—$R_{11}$, or straight or branched chain $C_1$–$C_{24}$alkyl which is interrupted by —O—, —S— or —$NR_{11}$ and which can be unsubstituted or substituted by —OH or —OCO—$R_{11}$, $C_5$–$C_{12}$ cycloalkyl which is unsubstituted or substituted by —OH, straight chain or branched $C_2$–$C_{18}$alkenyl which is unsubstituted or substituted by —OH, $C_7$–$C_{15}$aralkyl, —$CH_2$—CHOH—$R_{13}$ or glycidyl, $R_6$ is hydrogen, straight or branched chain $C_1$–$C_{24}$alkyl which is unsubstituted or substituted by one or more OH, $OR_4$ or $NH_2$ groups, or —$OR_6$ is —$(OCH_2CH_2)_wOH$ or —$(OCH_2CH_2)_wOR_{21}$ where w is 1 to 12 and $R_{21}$ is alkyl of 1 to 12 carbon atoms, $R_7$ and $R_8$ are independently hydrogen, alkyl of 1 to 18 carbon atoms, straight or branched chain $C_3$–$C_{18}$alkyl which is interrupted by —O—, —S— or —$NR_{11}$, $C_5$–$C_{12}$cycloalkyl, $C_6$–$C_{14}$aryl or $C_1$–$C_3$hydroxylalkyl, or $R_7$ and $R_8$ together with the N atom are a pyrrolidine, piperidine, piperazine or morpholine ring, when n is 2, $R_5$ is one of divalent radicals —O—$R_9$—O— or —$N(R_{11})$—$R_{10}$—$N(R_{11})$—, $R_9$ is $C_2$–$C_8$alkylene, $C_4$–$C_8$alkenylene, $C_4$alkynylene, cyclohexylene, straight or branched chain $C_4$–$C_{10}$alkylene which is interrupted by —O— or by —$CH_2$—CHOH—$CH_2$—O—$R_{14}$—O—$CH_2$—CHOH—$CH_2$—, $R_{10}$ being straight or branched chain $C_2$–$C_{12}$alkylene which may be interrupted by —O—, cyclohexylene, or

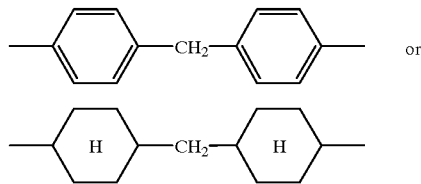

or or $R_{10}$ and $R_{11}$ with the two nitrogen atoms form a piperazine ring, $R_{14}$ is straight or branched chain $C_2$–$C_8$alkylene, straight or branched chain $C_4$–$C_{10}$alkylene which is interrupted by —O—, cycloalkylene, arylene or

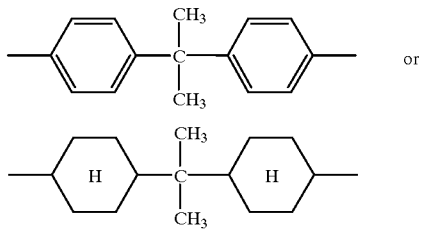

or where $R_7$ and $R_8$ are independently hydrogen, alkyl of 1 to 18 carbon atoms or $R_7$ and $R_8$ together are alkylene of 4 to 6 carbon atoms, 3-oxapentamethylene, 3-iminopentamethylene or 3-methyliminopentamethylene, $R_{11}$ is hydrogen, straight or branched chain $C_1$–$C_{18}$alkyl, $C_5$–$C_{12}$cycloalkyl, straight or branched chain $C_3$–$C_8$alkenyl, $C_6$–$C_{14}$aryl or $C_7$–$C_{15}$aralkyl, $R_{12}$ is straight or branched chain $C_1$–$C_{18}$alkyl, straight or branched chain $C_3$–$C_{18}$alkenyl, $C_5$–$C_{10}$cycloalkyl, $C_6$–$C_{16}$aryl or $C_7$–$C_{15}$aralkyl, $R_{13}$ is H, straight chain or branched $C_1$–$C_{18}$alkyl which is substituted by —$PO(OR_{12})_2$, phenyl which is unsubstituted or substituted by OH, $C_7$–$C_{15}$aralkyl or —$CH_2OR_{12}$, L is alkylene of 1 to 12 carbon atoms, alkylidene of 2 to 12 carbon atoms, benzylidene, p-xylylene, α,α, α',α'-tetramethyl-m-xylylene or cycloalkylidene, and T is —SO—, —$SO_2$—, —SO—E—SO—, —SO—E—$SO_2$— or —$SO_2$—E—$SO_2$—, where E is alkylene of 2 to 12 carbon atoms, cycloalkylene of 5 to 12 carbon atoms, or alkylene interrupted or terminated by cyclohexylene of 8 to 12 carbon atoms, which comprises reacting in a first step a compound corresponding to formula A, B, C or D wherein at least one of $G_1$, $G_1'$, $G_2$ or $G_2'$ is halogen, with an aliphatic, phenylalkyl or aromatic mercaptan of the formula $R_3SH$ or $R_3SM$ wherein $R_3$ is alkyl of 1 to 20 carbon atoms, —$(CH_2)_xCOOG_3$ where x is 1 to 18, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, and M is an alkali metal or an alkaline earth metal salt of said mercaptan, in an aprotic solvent at a temperature between 30 and 180° C. in the presence of an alkali metal or alkaline earth metal oxide, carbonate or hydroxide or an aminic compound to form, but not isolate, the compound corresponding to formula A, B, C or D wherein at least one of $G_1$, $G_1'$, $G_2$ or $G_2'$ is $R_3S$— and, in a second step, oxidizing said $R_3S$-substituted compound in an inert solvent at a temperature between 30 and 100° C. using 10% to 70% hydrogen peroxide and a catalyst selected from the oxides of Group VA and VIA metals of the periodic table in the presence of formic acid to give the desired $R_3SO_2$-substituted compound of formula A, B, C or D.

This process is illustrated as outlined below:

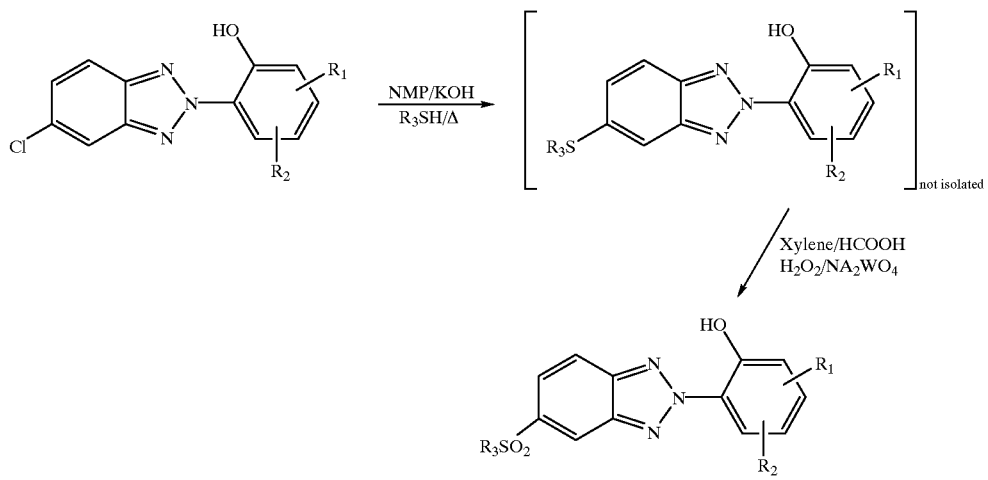

where $R_1$, $R_2$ and $R_3$ are as defined above.

The first step of this process involves the preparation, but not the isolation, of a compound of formula

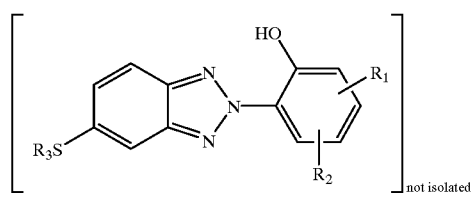

by reacting a 5-halo-substituted compound of the formula II

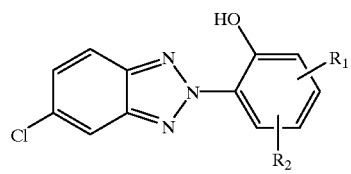

with an aliphatic, phenylalkyl or aromatic mercaptan or its alkali metal or alkaline earth metal salt of the formula $R_3SH$ or $R_3SM$ wherein $R_1$, $R_2$ and $R_3$ are defined above, in an aprotic solvent at a temperature between 30 and 180° C. in the presence of an alkali metal or alkaline earth metal oxide, carbonate or hydroxide or amine containing base.

The second step of this process involves the oxidation of the compound of formula

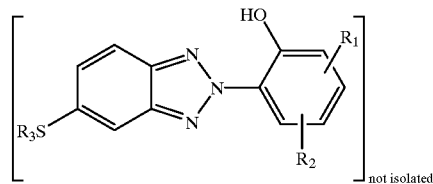

in an aromatic hydrocarbon solvent, such as xylene, at a temperature between 30 and 100° C., preferably between 50° C. and 95° C., using hydrogen peroxide of 10 to 70% concentration, preferably of 30 to 50% concentration, and sodium tungstate catalyst in the presence of formic acid to give the desired 5-sulfonyl compound of formula I

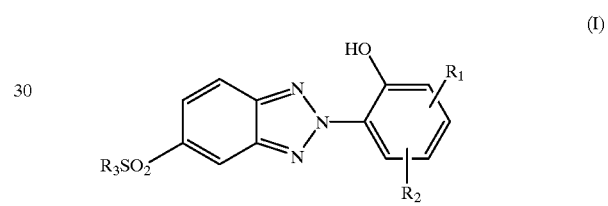

in good yield and purity.

In respect to the process parameters, the Step 1 aprotic solvents suitable for use include, but are not limited to, sulfones, lactams, amides and mixtures thereof. Specific examples of such solvents are sulfolane, N,N-dimethylformamide, N,N-dimethyl-acetamide, N-ethylcaprolactam, caprolactam, tetramethylurea, hexamethylphosphoramide, N,N-diethylenedipyrrolidine, N-methyl-2-pyrrolidone, pyrrolidone and mixtures thereof. The most preferred solvent is N-methyl-2-pyrrolidone.

The temperature of Step 1 used for optimum results include the range of 30–180° C. A preferred temperature range is 50–180° C.; and a most preferred range is 90–180° C. for Step 1.

The molar ratio of the sulfur-containing mercaptan compound to the halogen-substituted 2-(2-hydroxyphenyl)-2H-benzotriazole is in the range of about 0.75:1 to about 2:1; preferably about a 1:1 molar ratio of sulfur-containing compound per halogen atom. Of course, the preferred ratio would be about 1:2 for difunctional sulfur containing compounds to mono-halogen substituted benzotriazoles.

Optionally, the process of the instant invention can also be carried out in the presence of a basic compound selected from the group consisting of the alkali metal or alkaline earth metal carbonates, hydroxides or oxides, or amine compound or mixtures thereof in the presence of water or in the absence of water. Examples of such compounds include, but are not limited to, ammonium hydroxide, tetramethylammonium hydroxide, triethylamine, tributylamine, trihexylamine, sodium hydroxide, potassium hydroxide, lithium hydroxide, magnesium hydroxide, calcium hydroxide, calcium oxide, magnesium carbonate, sodium carbonate, potassium carbonate, calcium carbonate and mixtures thereof. The most preferred basic compound is potassium hydroxide.

The molar ratio of basic compound to halogen-substituted hydroxyphenylbenzotriazole is from about 0.5:1 to about 4:1. The preferred molar ratio is from about 1.5:1 to about 3:1.

The amount of solvent required in this process is that needed to dissolve the reactants adequately.

A different solvent is required at the end of Step 1 so as to avoid the need for any product isolation. The requirements of this inert solvent is that it sufficiently dissolves the product and is water immiscible. Typical solvents which can be used include, but are not limited to, methylene chloride, carbon tetrachloride, chloroform, heptane, octane, nonane, toluene, xylene(s), mesitylene, dibutyl ether and tetrahydrofuran. The preferred solvents for this non-isolation portion of the process are methylene chloride, carbon tetrachloride, heptane, octane, toluene and xylene(s) since they are stable to the oxidizing conditions of the subsequent step thus negating the need for another solvent during the oxidation step. The most preferred solvent is xylene which can be any of the three isomers or a mixture thereof.

The Step 1 neutralization can be done with any acid or acid producing agent capable of neutralizing the basic compound. The amount of acid is the amount required to effect that neutralization.

In the Step 2 oxidation, any oxidizing agent capable of oxidizing thioether derivatives to sulfonyl derivatives of the substituted 2-(2-hydroxyphenyl)-2H-benzotriazoles can be used. The most preferred oxidant system is hydrogen peroxide/formic acid or performic acid. The range of concentration for hydrogen peroxide is from about 10% to about 70%, preferably from about 30% to about 50%. Optionally, catalysts can be employed which would promote the desired oxidation. Such suitable catalysts include, but are not limited to, the oxides of Groups VA and VIA metals of the periodic table. The most preferred catalyst is sodium tungstate ($Na_2WO_4$).

The molar ratio of the oxidizing agent to the thioether derivative of the benzotriazole is in the range of from about 1:1 to about 8:1; preferably from 1:1 to 5:1.

The temperature range for the extraction in Step 2 is from about 30 to about 150° C. Of course, if temperatures are above 100° C., a pressure vessel is needed. The preferred temperature is 30–100° C.; most preferably 50–95° C.

It is clear that the major product prepared by the instant process is a sulfone, but some sulfoxide by-product may also be present especially if the process is run at lower temperatures, shorter reaction times and with a lower amount of hydrogen peroxide present.

Some representative halogen-substituted 2-(2-hydroxyphenyl)-2H-benzotriazoles, but not limited thereto, which may be used in the instant process are seen below:
1. 5-fluoro-2-(2,4-dihydroxyphenyl)-2H-benzotriazole;
2. 5-chloro-2-(2,4-dihydroxyphenyl)-2H-benzotriazole;
3. 5-bromo-2-(2,4-dihydroxyphenyl)-2H-benzotriazole;
4. 5-iodo-2-(2,4-dihydroxyphenyl)-2H-benzotriazole;
5. 5-chloro-2-(2-hydroxy-4-aminophenyl)-2H-benzotriazole;
6. 5-bromo-2-(2-hydroxy-4-aminophenyl)-2H-benzotriazole;
7. 5-chloro-2-(2-hydroxy-3-methyl-4-aminophenyl)-2H-benzotriazole;
8. 5-chloro-2-(2-hydroxy-3-n-octyl-4-aminophenyl)-2H-benzotriazole;
9. 5-fluoro-2-(2-hydroxy-5-methylphenyl)-2H-benzotriazole;
10. 5-chloro-2-(2-hydroxy-5-methylphenyl)-2H-benzotriazole;
11. 5-bromo-2-(2-hydroxy-5-methylphenyl)-2H-benzotriazole;
12. 5-iodo-2-(2-hydroxy-5-methylphenyl)-2H-benzotriazole;
13. 5-chloro-2-(2-hydroxy-5-tert-octylphenyl)-2H-benzotriazole;
14. 5-bromo-2-(2-hydroxy-5-tert-octylphenyl)-2H-benzotriazole;
15. 5-chloro-2-(2-hydroxy-3,5-di-tert-butylphenyl)-2H-benzotriazole;
16. 5-fluoro-2-(2-hydroxy-3,5-di-tert-butylphenyl)-2H-benzotriazole;
17. 5-bromo-2-(2-hydroxy-3,5-di-tert-butylphenyl)-2H-benzotriazole;
18. 5-iodo-2-(2-hydroxy-3,5-di-tert-butylphenyl)-2H-benzotriazole;
19. 5-chloro-2-(2-hydroxy-3,5-di-α-cumylphenyl)-2H-benzotriazole;
20. 5-fluoro-2-(2-hydroxy-3,5-di-α-cumylphenyl)-2H-benzotriazole;
21. 5-chloro-2-(2-hydroxy-3-α-cumyl-5-tert-octylphenyl)-2H-benzotriazole;
22. 5-bromo-2-(2-hydroxy-3-α-cumyl-5-tert-octylphenyl)-2H-benzotriazole;
23. 5-fluoro-2-(2-hydroxy-3-α-cumyl-5-tert-octylphenyl)-2H-benzotriazole;
24. 5-iodo-2-(2-hydroxy-3-α-cumyl-5-tert-octylphenyl)-2H-benzotriazole;
25. 5-chloro-2-(2-hydroxy-4-phenylphenyl)-2H-benzotriazole;
26. 5-fluoro-2-(2-hydroxy-4-phenylphenyl)-2H-benzotriazole;
27. 5-bromo-2-(2-hydroxy-4-phenylphenyl)-2H-benzotriazole;
28. 5-iodo-2-(2-hydroxy-4-phenylphenyl)-2H-benzotriazole;
29. 5-chloro-2-[2-hydroxy-3-tert-butyl-5-(3-hydroxypropyl)phenyl]-2H-benzotriazole;
30. 5-fluoro-2-[2-hydroxy-3-tert-butyl-5-(3-hydroxypropyl)phenyl]-2H-benzotriazole;
31. 5-bromo-2-[2-hydroxy-3-tert-butyl-5-(3-hydroxypropyl)phenyl]-2H-benzotriazole;
32. 5-iodo-2-[2-hydroxy-3-tert-butyl-5-(3-hydroxypropyl)phenyl]-2H-benzotriazole;
33. 3-(5-chloro-2H-benzotriazol-2-yl)-5-tert-butyl-4-hydroxyhydrocinnamic acid;
34. 3-(5-bromo-2H-benzotriazol-2-yl)-5-tert-butyl-4-hydroxyhydrocinnamic acid;
35. 3-(5-fluoro-2H-benzotriazol-2-yl)-5-tert-butyl-4-hydroxyhydrocinnamic acid;
36. 3-(5-iodo-2H-benzotriazol-2-yl)-5-tert-butyl-4-hydroxyhydrocinnamic acid;
37. 3-(5-chloro-2H-benzotriazol-2-yl)-5-α-cumyl-4-hydroxyhydrocinnamic acid;
38. 3-(5-bromo-2H-benzotriazol-2-yl)-5-α-cumyl-4-hydroxyhydrocinnamic acid;
39. 3-(5-fluoro-2H-benzotriazol-2-yl)-5-α-cumyl-4-hydroxyhydrocinnamic acid;
40. 3-(5-iodo-2H-benzotriazol-2-yl)-5-α-cumyl-4-hydroxyhydrocinnamic acid;
41. methyl 3-(5-chloro-2H-benzotriazol-2-yl)-5-tert-butyl-4-hydroxyhydrocinnamate;
42. methyl 3-(5-chloro-2H-benzotriazol-2-yl)-5-α-cumyl-4-hydroxyhydrocinnamate;
43. 5-chloro-2-(2-hydroxy-3,5-di-tert-amylphenyl)-2H-benzotriazole;

44. 5-fluoro-2-(2-hydroxy-3,5-di-tert-amylphenyl)-2H-benzotriazole;

45. 5-bromo-2-(2-hydroxy-3,5-di-tert-amylphenyl)-2H-benzotriazole;

46. 5-iodo-2-(2-hydroxy-3,5-di-tert-amylphenyl)-2H-benzotriazole;

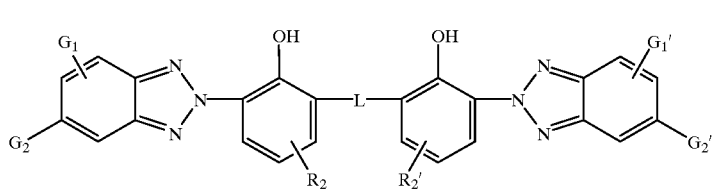

(D)

Compounds of formula D wherein
$G_1$ and $G_1'$ are each hydrogen;
$G_2$ and $G_2'$ are each fluoro, bromo, chloro or iodo;
$R_2$ and $R_2'$ are each methyl, tert-butyl or tert-octyl; and
L is methylene or $\alpha,\alpha,\alpha',\alpha'$-tetramethyl-m-xylylene.

A list of suitable sulfur-containing compounds include, but are not limited to, methyl mercaptan, sodium methanthiolate, n-butyl mercaptan, potassium butanethiolate, tert-butyl mercaptan, isobutyl mercaptan, thiophenol, sodium thiophenolate, 4-aminothiophenol, 4-cyanothiophenol, 4-hydroxythiophenol, 2-methoxythiophenol, 3-methoxythiophenol, 4-methoxythiophenol, octadecyl mercaptan, ethyl mercaptan, 2-mercaptoethanol, 3-mercaptopropionic acid, 2-mercaptoacetic acid, allyl mercaptan, 1,4-butanedithiol, 1,8-octanedithiol and 1,4-benzenedithiol.

The preferred compounds made by the instant process included, but are not limited to, a. 5-phenylsulfonyl-2-(2-hydroxy-3,5-di-tert-butylphenyl)-2H-benzotriazole;

b. 5-octylsulfonyl-2-(2-hydroxy-3,5-di-tert-butylphenyl)-2H-benzotriazole;

c. 5-phenylsulfonyl-2-(2-hydroxy-3,5-di-$\alpha$-cumylphenyl)-2H-benzotriazole;

d. 5-phenylsulfonyl-2-(2-hydroxy-3,5-di-$\alpha$-cumylphenyl)-2H-benzotriazole;

e. 5-phenylsulfonyl-2-(2-hydroxy-3-$\alpha$-cumyl-5-tert-octylphenyl)-2H-benzotriazole;

f. 5-octylsulfonyl-2-(2-hydroxy-3-$\alpha$-cumyl-5-tert-octylphenyl)-2H-benzotriazole;

g. 5-butylsulfonyl-2-(2-hydroxy-3-$\alpha$-cumyl-5-tert-octylphenyl)-2H-benzotriazole;

h. 5-ethylsulfonyl-2-(2-hydroxy-3-$\alpha$-cumyl-5-tert-octylphenyl)-2H-benzotriazole;

i. 5-n-dodecylsulfonyl-2-(2-hydroxy-3,5-di-tert-butylphenyl)-2H-benzotriazole;

j. 5,5'-sulfonyl-bis[2-(2-hydroxy-3-$\alpha$-cumyl-5-tert-octylphenyl)-2H-benzotriazole];

k. octyl 3-(5-phenylsulfonyl-2H-benzotriazo-2-yl)-5-tert-butyl-4-hydroxyhydrocinnamate;

l. 3-(5-phenylsulfonyl-2H-benzotriazo-2-yl)-5-tert-butyl-4-hydroxyhydrocinnamamide; or m. 5-phenylsulfonyl-2-[2-hydroxy-3-tert-butyl-5-(3-hydroxypropyl)phenyl]-2H-benzotriazole.

The following Examples are meant for illustrative purposes only and are not to be construed to limit the instant process in any manner whatsoever.

EXAMPLE 1

Synthesis of 5-phenylsulfonyl-2-(2-hydroxy-3,5-di-tert-butylphenyl)-2H-benzotriazole using two-step, one-pot process To a one-liter jacketed glass reactor are charged 150 g (0.42 mol) of 5-chloro-2-(2-hydroxy-3,5-di-tert-butylphenyl)-2H-benzotriazole and 275 g (2.78 mol) of N-methylpyrrolidinone. With agitation, the resultant slurry is heated to 90–95° C. At this time, 104.5 g (0.84 mol) of potassium hydroxide and 51.3 g (0.47 mol) of thiophenol are added. Heating is continued till the temperature reaches 170° C. while distilling off water through an overhead condenser. After two hours at 170° C., the temperature is cooled to 95° C. and the reaction mixture is neutralized with 120 g (0.49 mol) of hydrochloric acid. To this mixture is then added 100 g of water and 200 g of xylene. The brine layer is removed and the xylene phase is washed once with 150 g of water and separated off. The temperature of the xylene solution is reduced to 70° C. and 1.8 g (0.0055 mol) of sodium tungstate and 49.1 g (1.07 mol) of formic acid are added. To the reaction mixture is slowly added over a 60-minute period 83 g (1.22 mol) of 50% hydrogen peroxide at a rate such that a temperature of 70–80° C. is maintained. At the end of the addition of hydrogen peroxide, the reaction mass is held at 70–80° C. for 30 minutes and sampled for any residual sulfoxide by HPLC. After the reaction is complete, the xylene phase is then washed once with aqueous sodium sulfite solution and twice with water. The temperature is reduced to 65° C. and 500 g of methanol are added. The temperature is further reduced to 30–32° C. to induce crystallization. The yellow slurry formed is filtered and the solid material isolated is washed with 150 g of methanol. The yellow needles isolated are dried to constant weight in a vacuum oven to afford 172 g (88.6% yield based on the chloro-benzotriazole starting material) of the title compound. A HPLC scan of the product shows an assay of 99.3% of the desired sulfone compound.

EXAMPLE 2

Synthesis of 5-n-octylthio-2-(2-hydroxy-3,5-di-tert-butylphenyl)-2H-benzotriazole with isolation of step 1 demonstrating the yield enhancements of the instant process To a 500-mL, round-bottomed flask are charged 30 g (0.083 mol) of 5-chloro-2-(2-hydroxy-3,5-di-tert-butylphenyl)-2H-benzotriazole, 65 g (0.65 mol) of N-methyl-pyrrolidinone, 13.5 g (0.21 mol) of potassium hydroxide pellets and 25 g (0.16 mol) of n-octyl mercaptan are added. The mixture is agitated and the resultant slurry is heated to 170–175° C. and held at that temperature for 4.5 hours. The reaction mixture is then cooled to 120° C. at which time 150 g of xylene and 90 g of 10% aqueous hydrochloric acid are added. The brine layer is split off and the xylene phase at 90° C. is washed three times with water. Xylene is partially distilled under vacuum and then 80 g of methanol are added. The temperature of the reaction mixture is reduced to ambient temperature to induce crystallization. The yellow slurry formed is further cooled to 0–5° C. and filtered. The wetcake is washed with 100 g of cold methanol and dried to constant weight. The title compound is obtained as yellow needles in a yield of 37.7 g (97%). The structure of the product is verified by $^1$HNMR and mass spectroscopy.

EXAMPLE 3

Synthesis of 5-n-octylsulfonyl-2-(2-hydroxy-3,5-di-tert-butylphenyl)-2H-benzotriazole demonstrating the yield advantages of step 2

To a 500-mL round-bottom flask are charged 30 g (0.062 mol) of 5-n-octylthio-2-(2-hydroxy-3,5-di-tert-butylphenyl)-2H-benzotriazole, 35 g (0.28 mol) of xylene, 6.4 g (0.12 mol) of formic acid and 0.21 g (0.0006 mol) of sodium tungstate dihydrate. The reaction mixture is heated to 50° C. and 19 g (0.28 mol) of 50% hydrogen peroxide is then added dropwise over a one-hour period such that the reaction temperature remains between 70–80° C. After holding at this temperature for two hours, 100 g of water and 100 g of xylene are added. The aqueous layer is removed and the xylene phase is washed once with 10% aqueous sodium sulfite solution, 10% aqueous potassium carbonate solution, 10% aqueous sodium chloride solution and water. Xylene is partially stripped under vacuum and 50 g of methanol are added. The yellow solution is cooled to 0–5° C. and filtered after crystallization occurs. The wetcake is washed with 100 g of cold methanol and dried to a constant weight. The title compound is obtained as yellow needles in a yield of 30.1 g (97%). The structure of the product is verified by $^1$HNMR and mass spectroscopy.

EXAMPLE 4

Attempted Synthesis of 5-phenylsulfonyl-2-(2-hydroxy-3,5-di-tert-butylphenyl)-2H-benzotriazole Using Acetic Acid/Hydrogen Peroxide/Sodium Tungstate Using the general procedure of Example 3, 26.2 g (0.062 mol) of 5-phenylthio-2-(2-hydroxy-3,5-di-tert-butylphenyl)-2H-benzotriazole and 7.4 g (0.12 mol) of acetic acid are substituted for 5-n-octylthio-2-(2-hydroxy-3,5-di-tert-butylphenyl)-2H-benzotriazole and formic acid respectively. The products of this oxidation procedure are analyzed by HPLC and are as follows:

0.03% of 5-phenylsulfonyl-2-(2-hydroxy-3,5-di-tert-butylphenyl)-2H-benzotriazole;

60.1% of 5-phenylsulfinyl-2-(2-hydroxy-3,5-di-tert-butylphenyl)-2H-benzotriazole; and 34.9% of 5-phenylthio-2-(2-hydroxy-3,5-di-tert-butylphenyl)-2H-benzotriazole.

It is clear from the above that acetic acid and formic acid are not equivalent in this oxidation reaction and that the instant oxidizing system using formic acid is far superior to the system where formic acid is replaced with acetic acid.

EXAMPLE 5

Comparison of Instant and DesLauriers Processes

Table*

| Item | DesLauriers U.S. 5,319,091 | Instant |
|---|---|---|
| Step 1 Reaction Time | 6 hours | 2 hours |
| Step 1 React. Temp. °C. | 200 | 170–180 |
| Step 1 Yield % | 72.6[a] | 97[b] |
| Step 1 Isolation | required | not required |
| Step 1 Assay % | >99 | 99.9[c] |
| Step 2 Oxidant | MCPBA or $H_2O_2/H_2WO_4$ | $H_2O_2/Na_2WO_4$ and HCOOH |
| Step 2 Solvent | isopropanol or methylene chloride | xylene(s) |
| Step 2 React. Time | 3 hrs[d] or 12 hrs[e] | 30 minutes[f] |
| Step 2 React. Temp. °C. | 25[d] or 80[e] | 50–80 |
| Step 2 Yield % | 89.6[d] or 82.8[e] | 97[f] |
| Sulfide % Yield | 0.8[f] | 0[g] |
| Sulfoxide % Yield | 4.6[f] | 0[g] |
| Sulfone % Yield | 94.0[f] | 99.3[g] |

*[a]-U.S. 5,319,091, Example 1
[b]-Instant Example 2
[c]-Instant Example 1, Step 1
[d]-U.S. 5,319,091, Example 2
[e]-U.S. 5,319,091, Example 3
[f]-Instant Example 3
[g]-Instant Example 1, Step 2

EXAMPLES 6–11

When following the general procedure of Example 1, an equivalent amount of the benzotriazoles listed below are substituted for 5-chloro-2-(2-hydroxy-3,5-di-tert-butylphenyl)-2H-benzotriazole, the corresponding 5-phenylsulfonyl substituted compounds are prepared.

6. 5-fluoro-2-(2-hydroxy-3,5-di-α-cumylphenyl)-2H-benzotriazole;

7. 5-chloro-2-(2-hydroxy-3-α-cumyl-5-tert-octylphenyl)-2H-benzotriazole;

8. 3-(5-iodo-2H-benzotriazol-2-yl)-5-α-cumyl-4-hydroxyhydrocinnamic acid;

9. methyl 3-(5-chloro-2H-benzotriazol-2-yl)-5-tert-butyl-4-hydroxyhydrocinnamate;

10. methyl 3-(5-chloro-2H-benzotriazol-2-yl)-5-α-cumyl-4-hydroxyhydrocinnamate;

11. 5-chloro-2-(2-hydroxy-3,5-di-tert-amylphenyl)-2H-benzotriazole.

EXAMPLES 12–17

When following the general procedure of Examples 2 and 3, an equivalent amount of the benzotriazoles listed below are substituted for 5-chloro-2-(2-hydroxy-3,5-di-tert-butylphenyl)-2H-benzotriazole, the corresponding 5-octylsulfonyl substituted compounds are prepared.

12. 5-fluoro-2-(2-hydroxy-3,5-di-α-cumylphenyl)-2H-benzotriazole;

13. 5-chloro-2-(2-hydroxy-3-α-cumyl-5-tert-octylphenyl)-2H-benzotriazole;

14. 3-(5-iodo-2H-benzotriazol-2-yl)-5-α-cumyl-4-hydroxyhydrocinnamic acid;

15. methyl 3-(5-chloro-2H-benzotriazol-2-yl)-5-tert-butyl-4-hydroxyhydrocinnamate;

16. methyl 3-(5-chloro-2H-benzotriazol-2-yl)-5-α-cumyl-4-hydroxyhydrocinnamate;

17. 5-chloro-2-(2-hydroxy-3,5-di-tert-amylphenyl)-2H-benzotriazole.

What is claimed is:

1. A one-pot, two-step process for the preparation of a compound of formula A, B, C or D

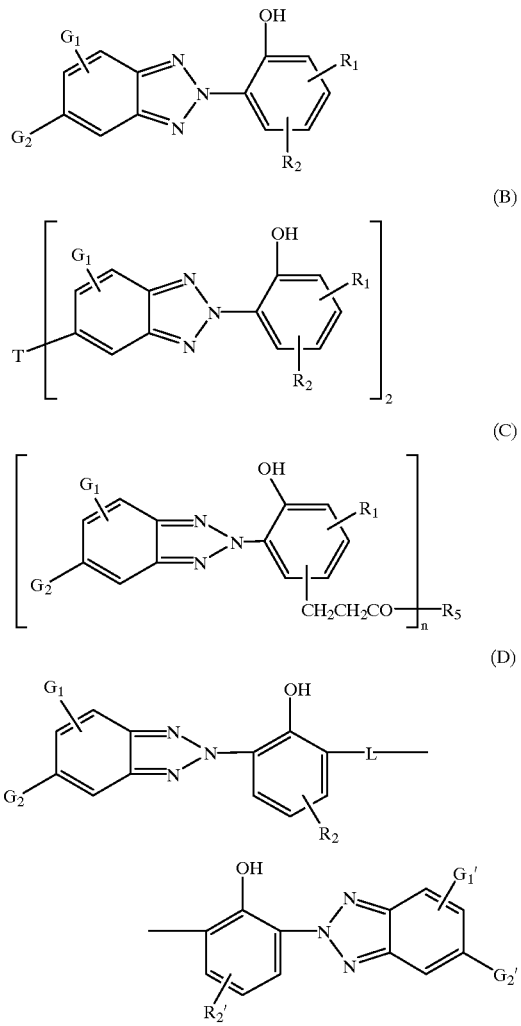

wherein
- $G_1$, $G_1'$, $G_2$ and $G_2'$ are independently hydrogen, halogen, nitro, cyano, $R_3SO-$, $R_3SO_2-$, $-COOG_3$, perfluoroalkyl of 1 to 12 carbon atoms, $-CO-G_3$, $-CO-NH-G_3$ or $-CO-N(G_3)_2$,
- $G_3$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms,
- with the proviso that at least one of $G_1$, $G_1'$, $G_2$ and $G_2'$ is $R_3SO_2$,
- $R_1$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms,
- $R_2$ and $R_2'$ are independently straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $R_2$ is hydroxyl or $-OR_4$ where $R_4$ is straight or branched chain alkyl of 1 to 24 carbon atoms; or said alkyl substituted by one or more $-OH$, $-OCO-R_{11}$, $-OR_4$, $-NCO$, $-NH_2$ or $-N(R_4)_2$ groups or mixtures thereof; or said alkyl or said alkenyl interrupted by one or more $-O-$, $-NH-$ or $-NR_4-$ groups or mixtures thereof and which can be unsubstituted or substituted by one or more $-OH$, $-OR_4$ or $-NH_2$ groups or

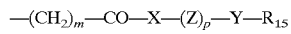

wherein
- X is $-O-$ or $-N(R_{16})-$,
- Y is $-O-$ or $-N(R_{17})-$,
- Z is $C_2-C_{12}$-alkylene, $C_4-C_{12}$-alkylene interrupted by one to three nitrogen atoms, oxygen atoms or a mixture thereof, or is $C_3-C_{12}$-alkylene, butenylene, butynylene, cyclohexylene or phenylene, each substituted by a hydroxyl group,
- m is zero, 1 or 2,
- p is 1, or p is also zero when X and Y are $-N(R_{16})-$ and $-N(R_{17})-$, respectively,
- $R_{15}$ is a group $-CO-C(R_{18})=C(H)R_{19}$ or, when Y is $-N(R_{17})-$, forms together with $R_{17}$ a group $-CO-CH=CH-CO-$, wherein $R_{18}$ is hydrogen or methyl, and $R_{19}$ is hydrogen, methyl or $-CO-X-R_{20}$, wherein $R_{20}$ is hydrogen, $C_1-C_{12}$-alkyl or a group of the formula,

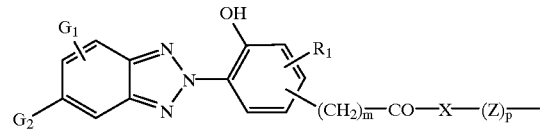

wherein the symbols $R_1$, X, Z, m and p have the meanings defined above, and $R_{16}$ and $R_{17}$ independently of one another are hydrogen, $C_1-C_{12}$-alkyl, $C_3-C_{12}$-alkyl interrupted by 1 to 3 oxygen atoms, or is cyclohexyl or $C_7-C_{15}$aralkyl, and $R_{16}$ together with $R_{17}$ in the case where Z is ethylene, also forms ethylene,
- n is 1 or 2,
- when n is 1, $R_5$ is Cl, $OR_6$ or $NR_7R_8$, or
- $R_5$ is $-PO(OR_{12})_2$, $-OSi(R_{11})_3$ or $-OCO-R_{11}$, or straight or branched chain $C_1-C_{24}$alkyl which is interrupted by $-O-$, $-S-$ or $-NR_{11}$ and which can be unsubstituted or substituted by $-OH$ or $-OCO-R_{11}$, $C_5-C_{12}$ cycloalkyl which is unsubstituted or substituted by $-OH$, straight chain or branched $C_2-C_{18}$alkenyl which is unsubstituted or substituted by $-OH$, $C_7-C_{15}$aralkyl, $-CH_2-CHOH-R_{13}$ or glycidyl,
- $R_6$ is hydrogen, straight or branched chain $C_1-C_{24}$alkyl which is unsubstituted or substituted by one or more OH, $OR_4$ or $NH_2$ groups, or $-OR_6$ is $-(OCH_2CH_2)_w$OH or $-(OCH_2CH_2)_wOR_{21}$ where w is 1 to 12 and $R_{21}$ is alkyl of 1 to 12 carbon atoms,
- $R_7$ and $R_8$ are independently hydrogen, alkyl of 1 to 18 carbon atoms, straight or branched chain $C_3-C_{18}$alkyl which is interrupted by $-O-$, $-S-$ or $-NR_{11}-$, $C_5-C_{12}$cycloalkyl, $C_6-C_{14}$aryl or $C_1-C_3$hydroxylalkyl, or $R_7$ and $R_8$ together with the N atom are a pyrrolidine, piperidine, piperazine or morpholine ring, when n is 2, $R_5$ is one of divalent radicals —O—$R_9$—O— or —N($R_{11}$)—$R_{10}$—N($R_{11}$)—, $R_9$ is $C_2$–$C_8$alkylene, $C_4$–$C_8$alkenylene, $C_4$alkynylene, cyclohexylene, straight or branched chain $C_4$–$C_{10}$alkylene which is interrupted by —O— or by —$CH_2$—CHOH—$CH_2$—O—$R_{14}$—O—$CH_2$—CHOH—$CH_2$—, $R_{10}$ being straight or branched chain $C_2$–$C_{12}$alkylene which may be interrupted by —O—, cyclohexylene, or

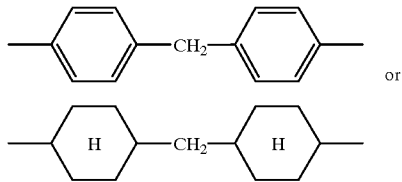

or $R_{10}$ and $R_{11}$ with the two nitrogen atoms form a piperazine ring, $R_{14}$ is straight or branched chain $C_2$–$C_8$alkylene, straight or branched chain $C_4$–$C_{10}$alkylene which is interrupted by —O—, cycloalkylene, arylene or

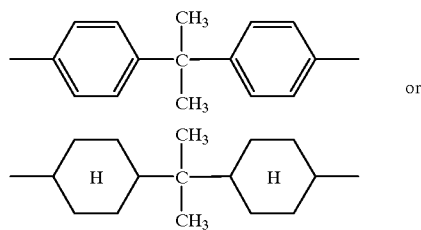

where $R_7$ and $R_8$ are independently hydrogen, alkyl of 1 to 18 carbon atoms or $R_7$ and $R_8$ together are alkylene of 4 to 6 carbon atoms, 3-oxapentamethylene, 3-iminopentamethylene or 3-methyliminopentamethylene, $R_{11}$ is hydrogen, straight or branched chain $C_1$–$C_{18}$alkyl, $C_5$–$C_{12}$cycloalkyl, straight or branched chain $C_3$–$C_8$alkenyl, $C_6$–$C_{14}$aryl or $C_7$–$C_{15}$aralkyl, $R_{12}$ is straight or branched chain $C_1$–$C_{18}$alkyl, straight or branched chain $C_3$–$C_{18}$alkenyl, $C_5$–$C_{10}$cycloalkyl, $C_6$–$C_{16}$aryl or $C_7$–$C_{15}$aralkyl, $R_{13}$ is H, straight chain or branched $C_1$–$C_{18}$alkyl which is substituted by —PO(O$R_{12}$)$_2$, phenyl which is unsubstituted or substituted by OH, $C_7$–$C_{15}$aralkyl or —$CH_2$O$R_{12}$, L is alkylene of 1 to 12 carbon atoms, alkylidene of 2 to 12 carbon atoms, benzylidene, p-xylylene, α,α,α',α'-tetramethyl-m-xylylene or cycloalkylidene, and T is —SO—, —SO$_2$—, —SO—E—SO—, —SO—E—SO$_2$— or —SO$_2$—E—SO$_2$—, where E is alkylene of 2 to 12 carbon atoms, cycloalkylene of 5 to 12 carbon atoms, or alkylene interrupted or terminated by cyclohexylene of 8 to 12 carbon atoms, which comprises reacting in a first step a compound corresponding to formula A, B, C or D wherein at least one of $G_1$, $G_1'$, $G_2$ or $G_2'$ is halogen, with an aliphatic, phenylalkyl or aromatic mercaptan of the formula $R_3SH$ or $R_3SM$ wherein $R_3$ is alkyl of 1 to 20 carbon atoms, —(CH$_2$)$_x$COO$G_3$ where x is 1 to 18, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, and M is an alkali metal or an alkaline earth metal salt of said mercaptan, in an aprotic solvent at a temperature between 30 and 180° C. in the presence of an alkali metal or alkaline earth metal oxide, carbonate or hydroxide or an aminic compound to form, but not isolate, the compound corresponding to formula A, B, C or D wherein at least one of $G_1$, $G_1'$, $G_2$ or $G_2'$ is $R_3S$— and, in a second step, oxidizing said $R_3S$-substituted compound in an inert solvent at a temperature between 30 and 150° C. using 10% to 70% hydrogen peroxide and a catalyst selected from the oxides of Group VA and VIA metals of the periodic table in the presence of formic acid to give the desired $R_3SO_2$-substituted compound of formula A, B, C or D.

2. A process according to claim 1 wherein the first step is run at a temperature of 50–180° C.

3. A process according to claim 2 wherein the first step is run at a temperature of 90–180° C.

4. A process according to claim 1 wherein the aprotic solvent for the first step is a sulfone, lactam or amide or mixtures thereof.

5. A process according to claim 4 wherein the solvent is sulfolane, N,N-dimethylformamide, N,N-dimethylacetamide, N-ethylcaprolactam, caprolactam, tetramethylurea, hexamethylphosphoramide, N,N-diethylenedipyrrolidine, N-methyl-2-pyrrolidone, pyrrolidone and mixtures thereof.

6. A process according to claim 5 wherein the solvent is N-methyl-2-pyrrolidone.

7. A process according to claim 1 wherein the molar ratio of sulfur-containing compound to the halogen-containing benzotriazole is from 0.75:1 to 2:1 based on one —SH group per halogen atom.

8. A process according to claim 7 wherein the molar ratio of sulfur-containing compound to the halogen-containing benzotriazole is 1:1.

9. A process according to claim 1 wherein the basic compound is ammonium hydroxide, tetramethylammonium hydroxide, triethylamine, tributylamine, trihexylamine, sodium hydroxide, potassium hydroxide, lithium hydroxide, magnesium hydroxide, calcium hydroxide, calcium oxide, magnesium carbonate, sodium carbonate, potassium carbonate, calcium carbonate or mixtures thereof.

10. A process according to claim 9 wherein the basic compound is potassium hydroxide.

11. A process according to claim 1 wherein the inert solvent for step 2 is methylene chloride, carbon tetrachloride, chloroform, heptane, octane, nonane, toluene, xylene(s), mesitylene, dibutyl ether and tetrahydrofuran.

12. A process according to claim 11 wherein the inert solvent for step 2 is methylene chloride, carbon tetrachloride, heptane, octane, toluene or xylene(s).

13. A process according to claim 1 wherein the catalyst for step 2 is sodium tungstate.

14. A process according to claim 1 wherein step 2 is carried out at a temperature of 30–100° C.

15. A process according to claim 14 wherein step 2 is carried out at a temperature of 50–95° C.

16. A process according to claim 1 wherein 30–50% hydrogen peroxide is used.

17. A process according to claim 1 wherein the compound prepared is
   a. 5-phenylsulfonyl-2-(2-hydroxy-3,5-di-tert-butylphenyl)-2H-benzotriazole;
   b. 5-octylsulfonyl-2-(2-hydroxy-3,5-di-tert-butylphenyl)-2H-benzotriazole;
   c. 5-phenylsulfonyl-2-(2-hydroxy-3,5-di-α-cumylphenyl)-2H-benzotriazole;
   d. 5-phenylsulfonyl-2-(2-hydroxy-3,5-di-α-cumylphenyl)-2H-benzotriazole;
   e. 5-phenylsulfonyl-2-(2-hydroxy-3-α-cumyl-5-tert-octylphenyl)-2H-benzotriazole;
   f. 5-octylsulfonyl-2-(2-hydroxy-3-α-cumyl-5-tert-octylphenyl)-2H-benzotriazole;
   g. 5-butylsulfonyl-2-(2-hydroxy-3-α-cumyl-5-tert-octylphenyl)-2H-benzotriazole;
   h. 5-ethylsulfonyl-2-(2-hydroxy-3-α-cumyl-5-tert-octylphenyl)-2H-benzotriazole;
   i. 5-n-dodecylsulfonyl-2-(2-hydroxy-3,5-di-tert-butylphenyl)-2H-benzotriazole;
   j. 5,5'-sulfonyl-bis[2-(2-hydroxy-3-α-cumyl-5-tert-octylphenyl)-2H-benzotriazole];
   k. octyl 3-(5-phenylsulfonyl-2H-benzotriazo-2-yl)-5-tert-butyl-4-hydroxyhydrocinnamate;
   l. 3-(5-phenylsulfonyl-2H-benzotriazo-2-yl)-5-tert-butyl-4-hydroxyhydrocinnamamide; or
   m. 5-phenylsulfonyl-2-[2-hydroxy-3-tert-butyl-5-(3-hydroxypropyl)phenyl]-2H-benzotriazole.

18. A process according to claim 17 wherein the compound prepared is
   a. 5-phenylsulfonyl-2-(2-hydroxy-3,5-di-tert-butylphenyl)-2H-benzotriazole; or
   b. 5-octylsulfonyl-2-(2-hydroxy-3,5-di-tert-butylphenyl)-2H-benzotriazole.

* * * * *